US010823716B2

(12) United States Patent
Lu

(10) Patent No.: US 10,823,716 B2
(45) Date of Patent: Nov. 3, 2020

(54) DETERMINING HYDROCARBON GAS MATURITY

(71) Applicant: Saudi Arabian Oil Company, Dhahran (SA)

(72) Inventor: Feng Hu Lu, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 129 days.

(21) Appl. No.: 15/868,782

(22) Filed: Jan. 11, 2018

(65) Prior Publication Data

US 2019/0212314 A1    Jul. 11, 2019

(51) Int. Cl.
    *E21B 49/08* (2006.01)
    *G01N 33/22* (2006.01)
    *G01N 33/00* (2006.01)
    *G01V 9/00* (2006.01)
    G01N 30/02 (2006.01)

(52) U.S. Cl.
    CPC ..... *G01N 33/0047* (2013.01); *E21B 49/0875* (2020.05); *G01N 33/225* (2013.01); *G01V 9/00* (2013.01); *G01V 9/007* (2013.01); *G01N 2030/025* (2013.01)

(58) Field of Classification Search
    CPC ............. G01N 33/225; G01N 33/0004; G01N 33/0047; G01V 9/007; E21B 49/087; E21B 49/0875
    See application file for complete search history.

(56) References Cited

U.S. PATENT DOCUMENTS 5,388,456 A * 2/1995 Kettel ............... G01V 9/007
    73/152.02
6,898,912 B2    5/2005 Bravinski

OTHER PUBLICATIONS

Lillis, P.G. et al. "Petroleum systems of the San Joaquin Basin Province—geochemical characteristics of gas types: Chapter 10 in Petroleum systems and geologic assessment of oil and gas in the San Joaquin Basin Province, California." U.S. Geological Survey. doi:10.3133/pp1713.ch10 (Year: 2008).*
Golding, S.D. et al. "Stable isotope geochemistry of coal bed and shale gas and related production waters: A review," International Journal of Coal Geology 120 (2013) 24-40 (Year: 2013).*
(Continued)

*Primary Examiner* — Christopher Adam Hixson
*Assistant Examiner* — Michelle Adams
(74) *Attorney, Agent, or Firm* — Fish & Richardson P.C.

(57) ABSTRACT

A measured wetness of and a $\delta^{13}C$ associated with a gas sample from a hydrocarbon formation is received wherein the wetness is a percentage of C2+ by mass. Calculated wetnesses of and $\delta^{13}C$ values associated with a plurality of gas samples taken from one or more analogous hydrocarbon reservoirs is received. Each wetness is calculated as a percentage of mass within the gas sample. The measured wetness received for the gas sample from among the calculated wetnesses is identified. A $\delta^{13}C$ is determined from among the $\delta^{13}C$ values that corresponds to the measured wetness of the gas sample. A gas maturity for the gas sample is determined using the determined $\delta^{13}C$.

20 Claims, 4 Drawing Sheets

(56) References Cited

OTHER PUBLICATIONS

Dolan, M.P. et al. "Calibrating Stable Carbon Isotopes of Reservoir Fluids As a Thermal Maturity Indicator," AAPG Search and Discovery Article #90092 © 2009 AAPG Rocky Mountain Section, Jul. 9-11, 2008, Denver, Colorado; Abstract only (Year: 2008).*

Zou, Caineng, "The Characteristics and Significance of Conventional and Unconventional Sinian-Lilurian Gas Systems in the Sichuan Basin, central China", Mar. 2015; 17 pages.

Faber, "Zur Isotopengeochemie gasförmiger Kohlenwasserstoffe," Geochemie, Erdöl Erdgas Kohle 103, May 1987, 9 pages.

Berner and Faber, "Maturity related mixing model for methane, ethane and propane, based on carbon isotopes," Org. Geochem. vol. 13, Sep. 25, 1988, 6 pages.

Whiticar, "Correlation of natural gases with their sources," AAPG Memoir, vol. 60, Jan. 1994, 23 pages.

Chung and Sacket, "Use of Stable Carbon Isotope Compositions of Pyrolytically Derived Methane as Maturity Indices for Carbonaceous Materials," Geochimica et Cosmochimica Acta, vol. 43, Dec. 1979, 10 pages.

International Search Report and Written Opinion issued in International Application No. PCT/US2019/012967 dated Apr. 26, 2019, 15 pages.

Gurgey et al., "Geochemical and isotopic approach to maturity/source/mixing estimations for nature gas and associated condensates in the Thrace Basin, NW, Turkey," Applied Geochemistry, Pergamon, Amsterdam, vol. 20, No. 11, Nov. 2005, 21 pages.

Xinyu et al., "Isotopic reversals with respect to maturity trends due to mixing of primary and secondary products in source rocks," Chemical Geology, Elsevier Science Publisher, vol. 339, Aug. 4, 2012, 8 pages.

Goddard et al., "Novel Gas Isotope Interpretation Tools to Optimize Gas Shale Production Contract: 08122-15," retrieved from URL http://citeseerx.ist.psu.edu/viewdoc/download?doi=10.1.1.397.4161&rep=rep1&type=pdf, retrieved on Apr. 11, 2019, available on or before Jun. 5, 2013, 90 pages.

Norville et al., "Carbon and hydrogen isotopic variations of natural gases in the Southeast Columbus basin offshore southeastern Trinidad, West Indies—clues to origin and maturity," Applied Geochemistry, Pergamon, Amsterdam, vol. 22, No. 9, Aug. 24, 2007, 9 pages.

Wang et al., "Geochemical characteristics and origin of nature gas in southern Jingbian fas field, Ordos Basin, China," Journal of Natural Gas Science and Engineering, Elsevier, Amsterdam, NL, vol. 46, Sep. 9, 2017, 11 pages.

Galimov, "Isotope organic geochemistry," Organic Geochemistry, 37(10), pp. 1200-1262, Apr. 2006, 63 pages.

Laughrey et al, "Limits to Hydrocarbon Stability in Deep Basins: Evidence from Stable Isotope Reversals and Noble Gas Geochemistry," EAGE Shale Workshop Conference, Nice, Paris, Apr. 2010, 2 pages.

* cited by examiner

DETERMINING HYDROCARBON GAS MATURITY

TECHNICAL FIELD

This disclosure relates to isotope geochemistry.

BACKGROUND

Carbon isotopes of natural gas can be utilized to calculate maturity of gas and source rocks found within a geologic formation. The maturity of either the gas or the source rock can be an indication of the suitability of the geologic formation for hydrocarbon production. As kerogen is progressively cracking, kinetic effects on isotopic fractionation result in two normal trends in light gaseous compounds from conventional gas fields. For example, the isotope ratio of carbon 13 ($\delta^{13}C$) over carbon 12 of each individual compound within a gas sample increases as maturity increases, and the $\delta^{13}C$ value of lighter compounds is lower than that of heavier compounds. The Faber equations, expressing a linear relationship between maturity and carbon isotope values, are widely used to calculate maturity.

SUMMARY

This disclosure describes technologies relating to determining hydrocarbon gas maturity.

An example implementation of the subject matter described within this disclosure is a first method with the following features. A measured wetness of and a carbon isotope ratio associated with a gas sample from a hydrocarbon formation is received wherein the wetness is a percentage of C2+ by mass. The carbon isotope ratio is a ratio of carbon-13 isotopes over carbon-12 isotopes. Calculated wetnesses of and carbon isotope ratios associated with a plurality of gas samples taken from one or more analogous hydrocarbon reservoirs is received. Each wetness is calculated as a percentage of mass within the gas sample. The measured wetness received for the gas sample from among the calculated wetnesses is identified. A carbon isotope ratio is determined from among the carbon isotope ratios that corresponds to the measured wetness of the gas sample. A gas maturity for the gas sample is determined using the determined carbon isotope ratio.

Aspects of the example first method, which can be combined with the example first method alone or in combination, incuse the following. The wetness of the gas sample is determined using a gas chromatograph.

Aspects of the example first method, which can be combined with the example first method alone or in combination, incuse the following. Determining a carbon isotope ratio from among the carbon isotope ratios includes determining an equation from the carbon isotope ratios and the wetnesses. The equation is used to create a reference line. The reference line is plotted on a plot with carbon isotope ratio on a Y-axis and wetness on an X-axis. The measured wetness is identified on the plot. A corresponding carbon isotope ratio is identified from the reference line.

Aspects of the example first method, which can be combined with the example first method alone or in combination, incuse the following. The equation is:

$$\delta^{13}C(C1) = -0.62W - 33.6$$

where $\delta^{13}C_{(C1)}$ is a carbon isotope ratio of carbon 13 over carbon-12 of methane in the gas sample, and "W" is a wetness expressed as a percentage.

Aspects of the example first method, which can be combined with the example first method alone or in combination, incuse the following. The equation is:

$$\delta^{13}C(C2) = -0.53W - 24.8$$

where $\delta^{13}C_{(C2)}$ is an isotope ratio of carbon-13 over carbon-12 of ethane in the gas sample, and "W" is a wetness expressed as a percentage.

Aspects of the example first method, which can be combined with the example first method alone or in combination, incuse the following. The equation is:

$$\delta^{13}C(C3) = -0.63W - 20.3$$

where $\delta^{13}C_{(C3)}$ is a an isotope ratio of carbon-13 over carbon-12 of propane in the gas sample, and "W" is a wetness expressed as a percentage.

Aspects of the example first method, which can be combined with the example first method alone or in combination, incuse the following. The wetness is determined to be within a specified range of values. An adjusted gas maturity is determined in response to determining that the wetness is within a specified range of values.

Aspects of the example first method, which can be combined with the example first method alone or in combination, incuse the following. The specified range of values is between 0% and 15%.

Aspects of the example first method, which can be combined with the example first method alone or in combination, incuse the following. Determining a gas maturity for the received gas sample includes using the following equation:

$$\delta^{13}C(C_1) = 15.4 \log_{10} VR_o - 41.3$$

where $\delta^{13}C$ ($C_1$) is a $\delta^{13}C$ of methane in the plurality of gas samples expressed in parts per thousand, and "$VR_o$" (vitrinite reflectance) correlates to a predicted $VR_o$ of the gas sample.

Aspects of the example first method, which can be combined with the example first method alone or in combination, incuse the following. Methane has a gas maturity and ethane has a gas maturity. A determined gas maturity of methane and a determined gas maturity of ethane are compared.

Aspects of the example first method, which can be combined with the example first method alone or in combination, incuse the following. A difference between the determined gas maturity of the methane and ethane is below a specified threshold. The determined gas maturity of ethane is ignored. a gas maturity of an entire gas sample is determined based on the determined maturity of methane.

An example implementation of the subject matter described within this disclosure is a second method with the following features. A test gas sample is received from a wellbore. A wetness is determined for the gas sample. A carbon isotope ratio associated with the gas sample is determined. The carbon isotope ratio is a ratio of carbon-13 isotopes to all carbon-12 isotopes. Carbon isotope ratios are received from multiple gas samples with a corresponding number of wetnesses for the gas samples. The gas samples are taken from one or more analogous hydrocarbon reservoirs. Each wetness is expressed as a percentage of mass within the gas sample. The wetness for the test gas sample is identified from among the wetnesses. A carbon isotope ratio is determined from among the carbon isotope ratios that corresponds to the wetness determined for the test gas sample. The carbon isotope ratio determined to be associated with the test gas sample is adjusted to equal the carbon isotope ratio determined from among the carbon isotope ratios. a gas maturity for the received gas sample is determined using the adjusted carbon isotope ratio.

Aspects of the example second method, which can be combined with the example second method alone or in combination, include the following. determining a carbon isotope ratio from among carbon isotope ratios includes determining an equation from the plurality of carbon isotope ratios. The equation is used to create a reference line.

Aspects of the example second method, which can be combined with the example second method alone or in combination, include the following. The equation is:

$$\delta^{13}C(C1)=-0.62W-33.6$$

where $\delta^{13}C_{(C1)}$ is a carbon isotope ratio of carbon-13 over carbon-12 of methane in the gas sample, and "W" is a wetness expressed as a percentage.

Aspects of the example second method, which can be combined with the example second method alone or in combination, include the following. The equation is:

$$\delta^{13}C(C2)=-0.53W-24.8$$

where $\delta^{13}C_{(C2)}$ is a carbon isotope ratio of carbon-13 over carbon-12 of ethane in the gas sample, and "W" is a wetness expressed as a percentage.

Aspects of the example second method, which can be combined with the example second method alone or in combination, include the following. Determining a gas maturity for the received gas sample includes using the following equation:

$$\delta^{13}C(C2)=22.6\ \text{Log}_{10}VR_o-32.2$$

where $\delta^{13}C\ (C_2)$ is a $\delta^{13}C$ of ethane in the plurality of gas samples expressed in parts per thousand, and "$VR_o$" correlates to a predicted $VR_o$ of the gas sample.

An example implementation of the subject matter described within this disclosure is a third method with the following features. A dataset comprising wetnesses and carbon isotope ratios of hydrocarbon gasses is received. The carbon isotope ratio is a ratio of carbon-13 to carbon-12. A reference line is determined from the dataset. The reference line is plotted on a plot. A sample wetness and a sample carbon isotope ratio determined from a received gas sample are plotted on a plot with the reference line to produce a plotted point. The plotted point is raised so that the carbon isotope ratio matches the reference line. An adjusted carbon isotope ratio is determined. A gas maturity for the received gas sample is determined using the adjusted carbon isotope ratio.

Aspects of the example third method, which can be combined with the example third method alone or in combination, include the following. A difference between the wetness and the reference line is determined to exceeds a specified threshold.

Aspects of the example third method, which can be combined with the example third method alone or in combination, include the following. The threshold is greater than or equal to a 10% difference.

Aspects of the example third method, which can be combined with the example third method alone or in combination, include the following. Determining a gas maturity for the received gas sample includes using the following equation:

$$\delta^{13}C(C3)=20.9\ \text{Log}_{10}VR_o-29.7$$

where $\delta^{13}C\ (C_3)$ is a $\delta^{13}C$ of propane in the plurality of gas samples expressed in parts per thousand, and "$VR_o$" correlates to a predicted $VR_o$ of the gas sample.

The details of one or more implementations of the subject matter described in this specification are set forth in the accompanying drawings and description. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

In some instances, carbon isotope ratios in light gas compounds from unconventional shale gas do not change linearly. Instead, the linear trend reverses as maturity increases in certain instances. The phenomena can occur in unconventional tight shale, sandstone, and in conventional gas fields when maturity is high or over mature. In the context of this disclosure, high maturity can be at least $R_0=2.0\%$ for example. In an unconventional reservoir, when $R_0>2.0\%$, an isotope reversal can occur. Over mature gas, in the context of this disclosure, $R_0>3\%$. However, this range can extend between 2.5% to 3.5% depending on the reservoir. When isotopic reversal occurs, the Faber equations are no longer applicable; maturity cannot be calculated by using isotopes from these gases and the Faber equations directly.

This disclosure relates to correcting reversed carbon isotopes of gases, and then applying the corrected isotope values to the Faber equations to calculate gas maturity using a corrected isotope ratio. To do so, a relationship between wetness and carbon isotopes is established. As maturity increases, wetness of natural gas decreases. As a result, wetness can be used as an indicator for maturity. As wetness decreases, carbon isotope ratios generally increase based on data from conventional and unconventional gas fields. When in the region of high wetness (For example, wetness>15%) and low maturity, carbon isotopes of methane (C1), ethane (C2), and propane (C3) increase linearly as wetness decreases. As wetness continuously decreases, C-isotopes of C1, C2, and C3 generally increase, but isotope reversal occurs particularly when wetness is <7%. That is, rather than C-isotope ratios increasing, C-isotope ratios drop or reverse the increasing trend around the aforementioned wetness. If the reversed isotopes were applied to the Faber equations, the resulting maturity would be calculated much lower, and the gas maturity would be severely under estimated.

Figure 1:
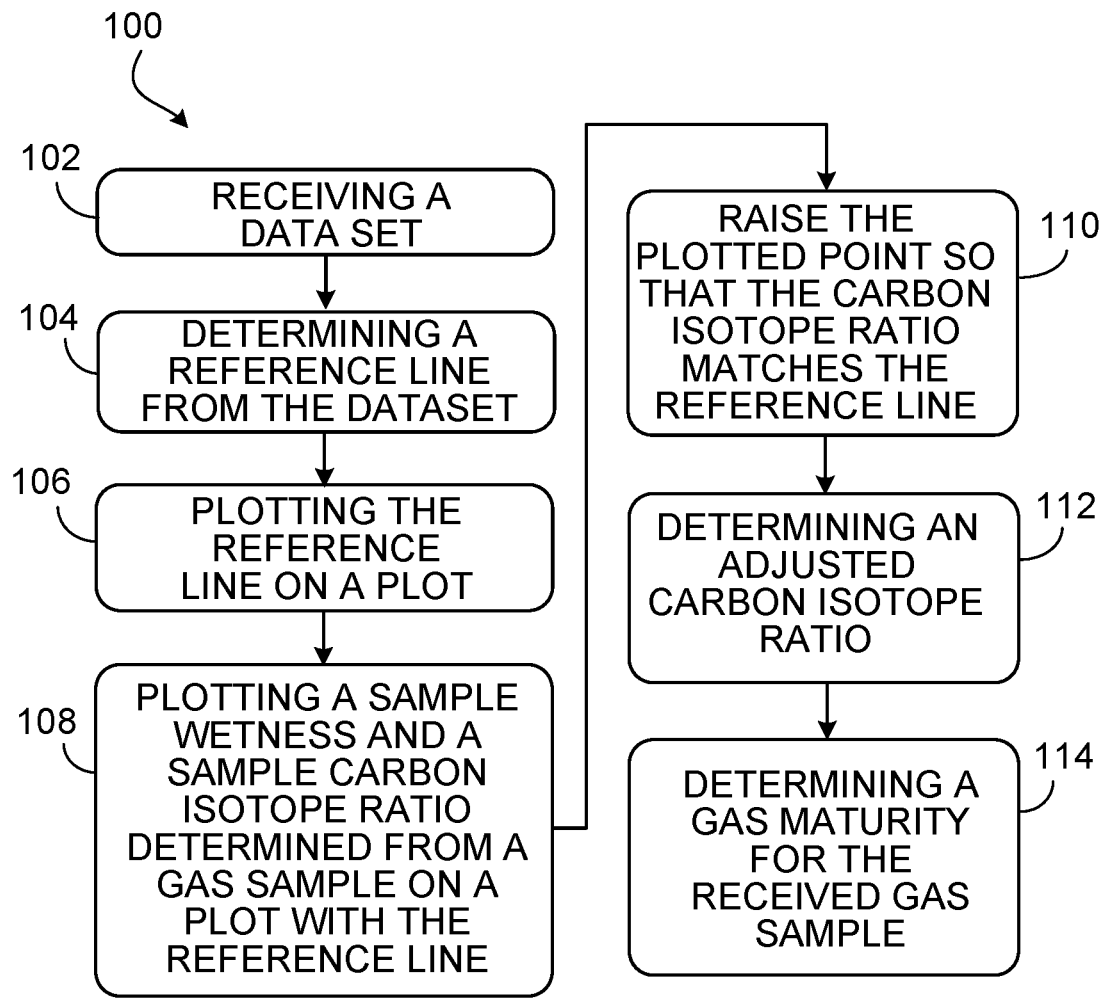
FIG. 1 is a flowchart of an example method that can be used with aspects of this disclosure.

FIG. 1 is a flowchart of an example method 100 that can be used with aspects of this disclosure. At 102, a dataset is received. The received dataset includes multiple calculated wetnesses of multiple gas samples and multiple carbon isotope ratios associated with the same multiple gas samples. The gas samples have been taken from one or more analogous hydrocarbon reservoirs. In the context of this disclosure, analogous fields often have the same geologic era and sedimentary rocks, for example all of the rocks are Paleozoic rocks or Mesozoic rocks. Each wetness can be expressed as a percentage that is calculated as a mass percentage of C2+ within the gas sample. The carbon isotope ratio ($\delta^{13}C$) is a ratio of carbon-13 isotopes over carbon-12 isotopes.

At 104, a reference line is determined from the dataset. An equation is determined from the dataset of multiple carbon isotope ratios and multiple wetnesses. The equation is used to create a reference line. The reference line is also based on the data falling the low maturity territory where the Faber equations can be applied. In another word, the line is extrapolated from the low maturity territory. Whereas data in the reversed territory are randomly distributed, even they form a line(s)

In one example, for methane, the equation being used to create a reference line is as follows:

$$\delta^{13}C(C1) = -0.62W - 33.6 \quad (EQ. 1)$$

where $\delta^{13}C_{(C1)}$ is an isotope ratio of carbon 13 over carbon 12 of methane in the gas sample, and "W" is a wetness expressed as a percentage.

In one example, for ethane, the equation being used to create a reference line is as follows:

$$\delta^{13}C(C2) = -0.53W - 24.8 \quad (EQ. 2)$$

where $\delta^{13}C_{(C2)}$ is an isotope ratio of carbon 13 over carbon 12 of ethane in the gas sample, and "W" is a wetness expressed as percentage.

In one example, for propane, the equation being used to create a reference line is as follows:

$$\delta^{13}C(C3) = -0.63W - 20.3 \quad (EQ. 3)$$

where $\delta^{13}C_{(C3)}$ is an isotope ratio of carbon 13 over carbon 12 of propane in the gas sample, and "W" is a wetness expressed as percentage.

Figure 2A:
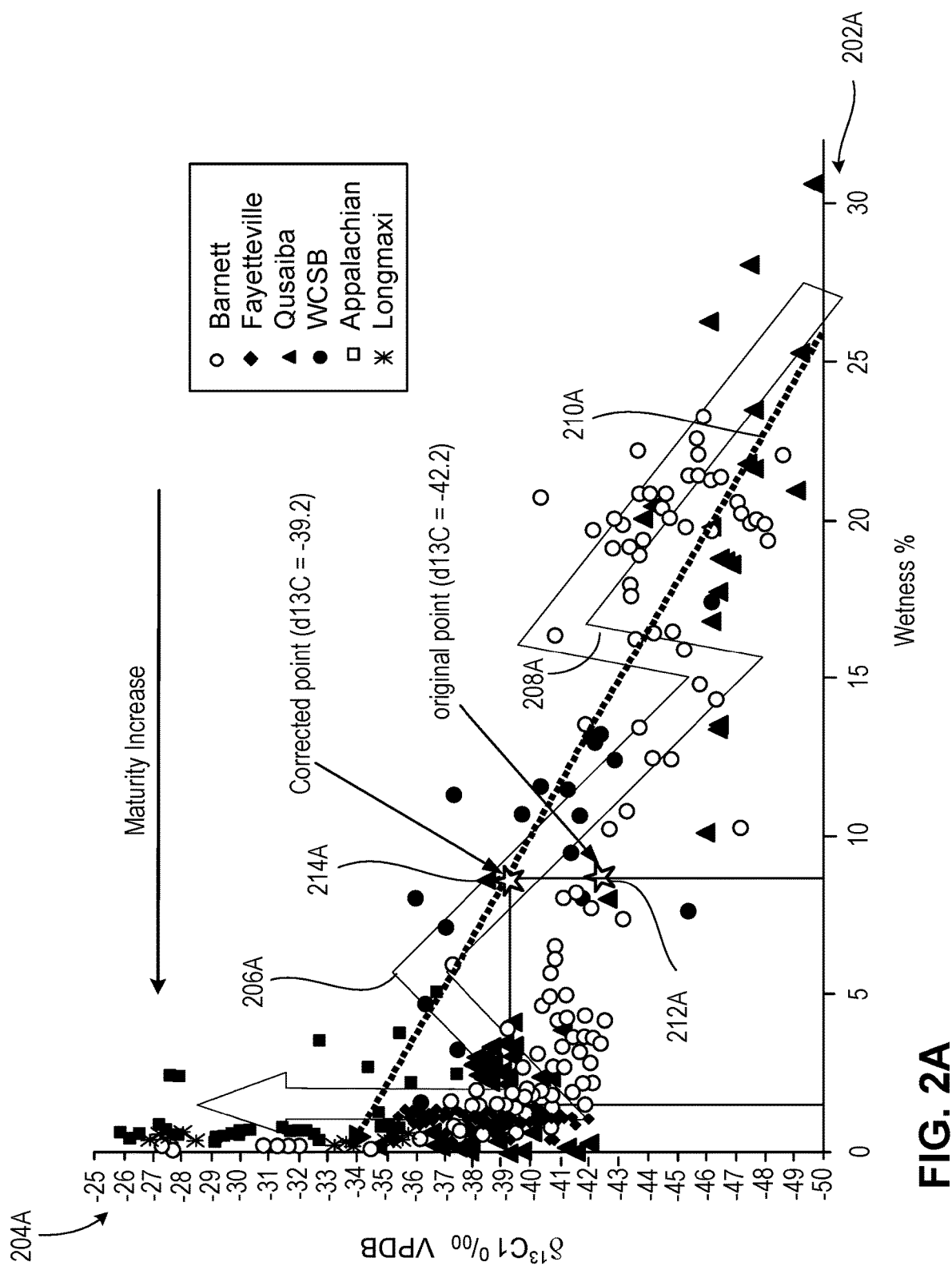
FIGS. 2A-2C are example plots that can be used with aspects of this disclosure.

At 106, the reference line is plotted on a plot with carbon isotope ratio on a Y-axis and wetness on an X-axis. Examples of such plotted reference lines can be seen in FIGS. 2A-2C. FIG. 2A is an example plot with a reference line for methane gas. The plot includes various data points from analogous reservoirs. A first methane isotopic reversal 206A occurs near a wetness of substantially 5%. A second methane isotopic reversal 208A occurs near a wetness of substantially 15%. A methane reference line 210A is formed through the data. In some implementations, the methane reference line can match up with EQ. 1.

Figure 2B:
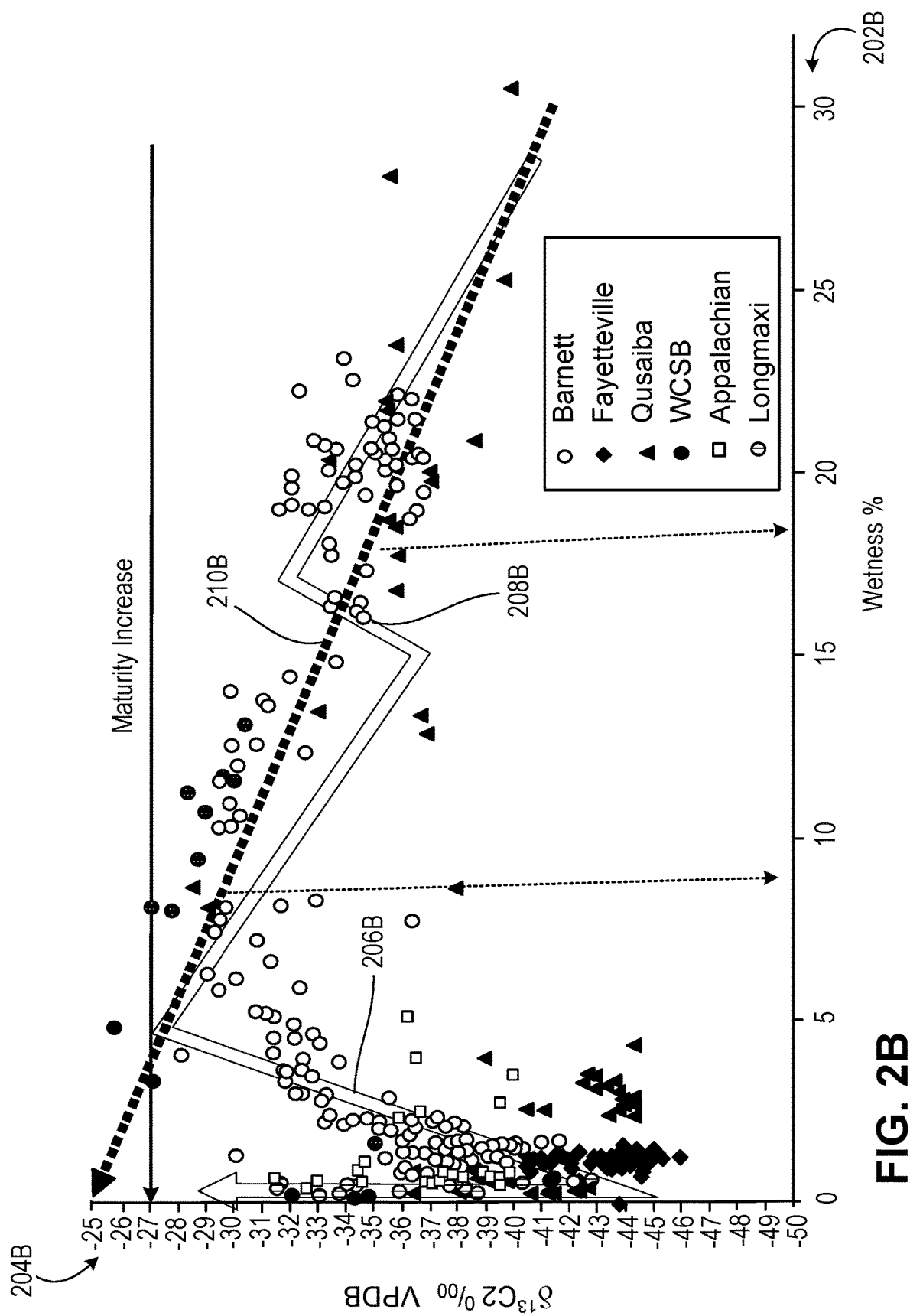

FIG. 2B is an example plot with a reference line for ethane gas. The plot includes various data points from analogous reservoirs. A first ethane isotopic reversal 206B occurs near a wetness of substantially 5%. A second ethane isotopic reversal 208B occurs near a wetness of substantially 15%. An ethane reference line 210B is formed through the data. In some implementations, the ethane reference line can match up with EQ. 2.

Figure 2C:
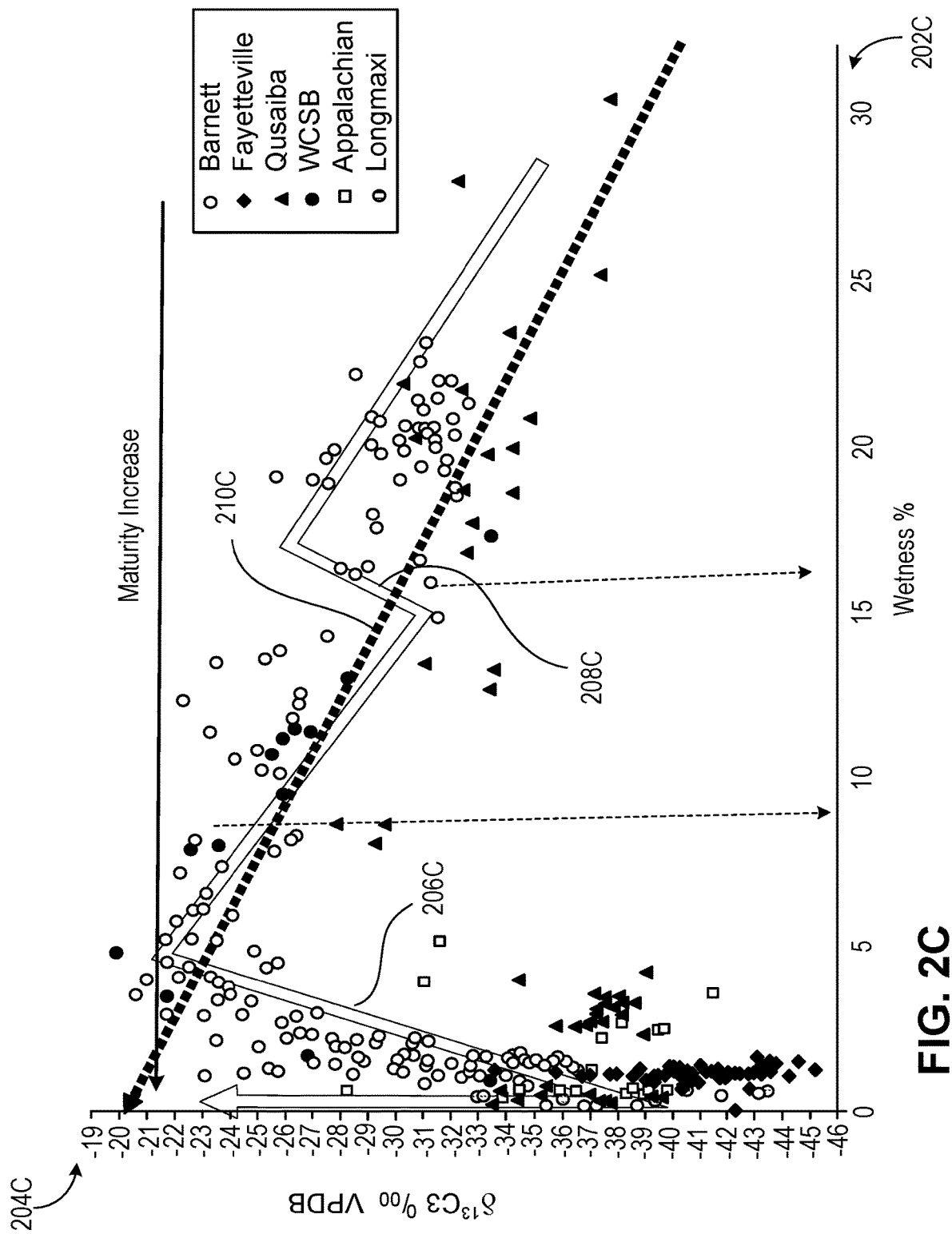

FIG. 2C is an example plot with a reference line for propane gas. The plot includes various data points from analogous reservoirs. A first propane isotopic reversal 206C occurs near a wetness of substantially 5%. A second propane isotopic reversal 208C occurs near a wetness of substantially 15%. A propane reference line 210C is formed through the data. In some implementations, the ethane reference line can match up with EQ. 3.

A gas sample is received from either an exploration well or a production well. The wetness of the gas sample and the carbon isotope ratio of the gas sample are determined with a gas chromatograph and isotope ratio mass spectrometer, respectively. As with the dataset, the wetness can be expressed as a mass percentage of C2+ within the sample (Note: wetness is calculated by this equation—wetness %=100×C2+/C1+-sum of C2, C3, C4 . . . over sum of C1, C2, C3 . . . ), while the carbon isotope ratio is a ratio of carbon-13 over carbon-12 expressed as $\delta^{13}C$ of one gas compound, e.g., $\delta^{13}C1$, $\delta^{13}C2$, $\delta^{13}C3$ . . . within a gas sample. At 108 (FIG. 1), a sample wetness and a sample carbon isotope ratio, both determined from the received gas sample, are plotted on a plot with the reference line to produce a plotted point. For example, the sample wetness and sample carbon isotope ranges can be plotted on the plots illustrated in FIG. 2A, FIG. 2B, FIG. 2C, or a combination of the plots. The wetness and carbon isotope ratios can be determined for multiple alkanes (methane, ethane, propane, etc.) with a single gas sample obtained from a wellbore.

As shown in FIG. 2A, the sample point 212A can be plotted on the plot based on the wetness and carbon isotope ratio determined from the gas sample. In other words, the measured wetness received for the gas sample is identified and corresponds to a wetness from among the multiple wetness in the dataset.

At 110, the plotted point 212A is raised along the Y-Axis to match the reference line to produce the adjusted point 214A. In other words, a wetness that matches that of the sample, from the multiple wetnesses within the dataset, is determined; then, a corresponding isotope ratio from the reference line is determined. That is, a carbon isotope ratio corresponding to the adjusted point 214A, from among the multiple carbon isotope ratios found within the dataset, is determined.

In some instances, the previously described adjustment is done after determining that the wetness is smaller than a specified threshold. For example, the specified threshold can be less than or equal to 15%. In some instances, the specified threshold can be less than or equal to 10%. When wetness gets small, gas gets drier and isotopes start to be reversed. The thresholds described are based on statistic data of unconventional gases collected from different fields as shown including those FIGS. 2A, 2B, and 2C. If the adjustment is made, then at 112, an adjusted carbon isotope ratio is determined in response to determining that the wetness is less than the specified threshold. In other words, the carbon isotope ratio determined to be associated with the test gas sample is adjusted to equal the carbon isotope ratio determined from among the multiple carbon isotope ratios of the dataset.

At 114, a gas maturity of the gas sample is determined based on the adjusted carbon isotope ratio. The maturity can be determined for individual alkanes, such as methane, ethane, and propane using linear equations similar to the Faber equations (EQ. 4-6). For example, a gas maturity of methane for the received gas sample can be determined with the following equation:

$$\delta^{13}C(C_1) = 15.4 \, \text{Log}_{10} VR_o - 41.3 \quad (EQ. 4)$$

wherein $\delta^{13}(C_1)$ is a $\delta^{13}C$ of methane in the plurality of gas samples expressed in parts per thousand, and "$VR_o$" (vitrinite reflectance) correlates to a predicted $VR_o$ of the gas sample. In another example, a gas maturity of ethane for the received gas sample can be determined with the following equation:

$$\delta^{13}C(C_2) = 22.6 \, \text{Log}_{10} VR_o - 32.2 \quad (EQ. 5)$$

wherein $\delta^{13}C(C_2)$ is a $\delta^{13}C$ of ethane in the plurality of gas samples expressed in parts per thousand, and "$VR_o$" correlates to a predicted $VR_o$ of the gas sample. In another example, a gas maturity of propane for the received gas sample can be determined with the following equation:

$$\delta^{13}C(C_3) = 20.9 \, \text{Log}_{10} VR_o - 29.7 \quad (EQ. 6)$$

wherein $\delta^{13}C(C_3)$ is a $\delta^{13}C$ of propane in the plurality of gas samples expressed in parts per thousand, and "$VR_o$" correlates to a predicted $VR_o$ of the gas sample.

As previously described, methane can have a gas maturity, ethane can have a gas maturity, and propane can have a gas maturity. A maturity for all three gases can be determined from a single gas sample obtained from a well. In some instances, comparing a determined gas maturity of methane, a determined gas maturity of ethane, and a determined maturity of propane can be helpful for verifying results. However, in some instances, the difference between the determined gas maturities of the various alkanes is above a specified threshold. For example, the difference between $\delta^{13}C$ (C1) and $\delta^{13}C$ (C2) or $\delta^{13}C$ (C3) could be up to 0.5% or more. In such an instance, when calculating the maturity in the isotopic reversal range, the methane maturity is the most reliable, and the determined maturity of the other alkanes (ethane and propane) can be ignored when determining a maturity of the gas sample. That is, a gas maturity of the entire gas sample is determined based on the determined maturity of methane.

While this specification contains many specific implementation details, these should not be construed as limitations on the scope of what may be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the implementations previously described should not be understood as requiring such separation in all implementations, and it should be understood that the described components and systems can generally be integrated together in a single product or packaged into multiple products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. For example, EQ. 1-3 may be universally applicable. In such an instance, when a gas has reversed isotopes and wetness less than 15%, particularly less than 10%, then no need to plot data and develop equations. These equations may be programmed and plotted with grids. In such an instance a sample isotope value plotted on the figure; then the value point can be vertically moved to the line and obtained a corrected value which can be then applied to the Faber equations.

What is claimed is:

1. A method comprising:
    receiving a measured wetness of and a measured $\delta^{13}C$ value associated with a test gas sample from a hydrocarbon formation, wherein the measured wetness is a percentage of $C_{2+}$ by mass;
    receiving a plurality of calculated wetnesses of and a plurality of calculated $\delta^{13}C$ values associated with a plurality of gas samples taken from one or more analogous hydrocarbon reservoirs that are analogous to the hydrocarbon formation, each of the plurality of calculated wetnesses being a percentage of $C_{2+}$ by mass;
    identifying, from among the plurality of calculated wetnesses, the measured wetness received for the test gas sample;
    determining a corresponding $\delta^{13}C$ value from among the plurality of calculated $\delta^{13}C$ values that corresponds to the measured wetness of the test gas sample;
    determining a predicted sample $VR_o$ (vitrinite reflectance) for the test gas sample based on the corresponding $\delta^{13}C$ value and a correlation of $\delta^{13}C$ values to $VR_o$ values, the $VR_o$ values correlating with gas maturity; and
    producing hydrocarbons from the hydrocarbon formation based on gas maturity.

2. The method of claim 1, further comprising determining the measured wetness of the test gas sample by a gas chromatograph.

3. The method of claim 1, wherein determining the corresponding $\delta^{13}C$ value from among the plurality of calculated $\delta^{13}C$ values comprises:
    determining an equation to best fit the plurality of calculated $\delta^{13}C$ values and the plurality of calculated wetnesses, the equation being used to create a reference line;
    plotting the reference line on a plot with a Y-axis representative of a range of the plurality of calculated $\delta^{13}C$ values and an X-axis representative of a range of the plurality of calculated wetnesses, the measured wetness being identified on the plot; and
    identifying a $\delta^{13}C$ value corresponding to the measured wetness from the reference line.

4. The method of claim 3, wherein the equation is:

$$\delta^{13}C(C_1)=-0.62W-33.6$$

where $\delta^{13}C$ ($C_1$) corresponds to values of $\delta^{13}C$ of methane in the plurality of gas samples, and "W" corresponds to the plurality of calculated wetnesses of the plurality of gas samples.

5. The method of claim 3, wherein the equation is:

$$\delta^{13}C(C_2)=-0.53W-24.8$$

where $\delta^{13}C$ ($C_2$) corresponds to values of $\delta^{13}C$ of ethane in the plurality of gas samples, and "W" corresponds to the plurality of calculated wetnesses of the plurality of gas samples.

6. The method of claim 3, wherein the equation is:

$$\delta^{13}C(C_3)=-0.63W-20.3$$

where $\delta^{13}C$ ($C_3$) corresponds to values of $\delta^{13}C$ of propane in the plurality of gas samples, and "W" corresponds to the plurality of calculated wetnesses of the plurality of gas samples.

7. The method of claim 1, further comprising:
    determining that the measured wetness is within a specified range of values, the specified range of values indicative of an isotopic reversal.

8. The method of claim 7, wherein the specified range of values for the measured wetness is between 0% and 15%.

9. The method of claim 1, wherein the correlation of $\delta^{13}C$ values to $VR_o$ values used for determining the predicted sample $VR_o$ for the test gas sample comprises the following equation:

$$\delta^{13}C(C_1)=15.4 \log_{10}VR_o-41.3$$

wherein $\delta^{13}C$ ($C_1$) is $\delta^{13}C$ of methane.

10. The method of claim 1, wherein the test gas sample comprises methane and ethane, methane within the test gas sample has a predicted methane sample $VR_o$ and ethane within the test gas sample has a predicted ethane sample $VR_o$, and the method further comprises comparing the predicted methane sample $VR_o$ and the predicted ethane sample $VR_o$.

11. The method of claim 10, wherein a difference between the predicted methane sample $VR_o$ and the predicted ethane sample $VR_o$ is below a specified threshold, the method further comprising:
    ignoring the predicted ethane sample $VR_o$; and
    determining the predicted sample $VR_o$ based on the predicted methane sample $VR_o$.

12. A method comprising:
    receiving a test gas sample from a wellbore within a test hydrocarbon formation;
    determining a measured wetness of the test gas sample;
    determining a measured $\delta^{13}C$ value associated with the test gas sample;
    receiving a plurality of calculated $\delta^{13}C$ values from a plurality of gas samples with a corresponding plurality of calculated wetnesses of the plurality of gas samples, wherein the plurality of gas samples are taken from one or more analogous hydrocarbon formations that are analogous to the test hydrocarbon formation;
    identifying, from the plurality of calculated wetnesses, the measured wetness of the test gas sample;
    determining a corresponding $\delta^{13}C$ value from among the plurality of calculated $\delta^{13}C$ values that corresponds to the measured wetness of the test gas sample;
    adjusting the measured $\delta^{13}C$ value to equal the corresponding $\delta^{13}C$ value to provide an adjusted $\delta^{13}C$ value;
    determining a predicted sample $VR_o$ (vitrinite reflectance) for the test gas sample based on the adjusted $\delta^{13}C$ value and a correlation of $\delta^{13}C$ values to $VR_o$ values, the $VR_o$ values correlating with gas maturity; and
    producing hydrocarbons from the test hydrocarbon formation based on gas maturity.

13. The method of claim 12, wherein determining the corresponding $\delta^{13}C$ value from among the plurality of calculated $\delta^{13}C$ values comprises determining a best-fit equation from the plurality of calculated $\delta^{13}C$ values and the plurality of calculated wetnesses, the best-fit equation being used to create a reference line.

14. The method of claim 13, wherein the best-fit equation is:

$$\delta^{13}C(C_1)=-0.62W-33.6$$

where $\delta^{13}C$ ($C_1$) corresponds to values of $\delta^{13}C$ of methane in the plurality of gas samples, and "W" corresponds to the plurality of calculated wetnesses of the plurality of gas samples.

15. The method of claim 13, wherein the best-fit equation is:

$$\delta^{13}C(C_2)=-0.53W-24.8$$

where $\delta^{13}C$ ($C_2$) corresponds to values of $\delta^{13}C$ of ethane in the plurality of gas samples, and "W" corresponds to the plurality of calculated wetnesses of the plurality of gas samples.

16. The method of claim 12, wherein the correlation of $\delta^{13}C$ values to $VR_o$ values used for determining the predicted sample $VR_o$ for the test gas sample comprises the following equation:

$$\delta^{13}C(C_2)=22.6 \log_{10}VR_o-32.2$$

wherein $\delta^{13}C$ ($C_2$) is $\delta^{13}C$ of ethane.

17. A method comprising:
    receiving a dataset comprising calculated wetnesses of and calculated $\delta^{13}C$ values associated with hydrocarbon gasses;
    determining a reference line from the dataset;
    plotting the reference line on a plot;
    plotting a sample wetness of and a sample $\delta^{13}C$ value associated with a received gas sample received from a hydrocarbon formation on the plot with the reference line to produce a plotted point;
    increasing a $\delta^{13}C$ value of the plotted point to provide an adjusted plotted point so that a $\delta^{13}C$ value of the adjusted plotted point matches the reference line;
    determining an adjusted $\delta^{13}C$ value from the adjusted plotted point, wherein the adjusted $\delta^{13}C$ value is the $\delta^{13}C$ value of the adjusted plotted point;
    determining a predicted sample $VR_o$ (vitrinite reflectance) for the received gas sample based on the adjusted $\delta^{13}C$ value and a correlation of $\delta^{13}C$ values to $VR_o$ values, the $VR_o$ values correlating with gas maturity; and
    producing hydrocarbons from the hydrocarbon formation based on gas maturity.

18. The method of claim 17, further comprising determining that a difference between the sample wetness and the reference line exceeds a specified threshold.

19. The method of claim 18, wherein the threshold is greater than or equal to a 10% difference.

20. The method of claim 17, wherein the correlation of $\delta^{13}C$ values to $VR_o$ values used for determining the predicted sample $VR_o$ for the received gas sample comprises the following equation:

$$\delta^{13}C(C_3)=20.9 \log_{10}VR_o-29.7$$

wherein $\delta^{13}C$ ($C_3$) is $\delta^{13}C$ of propane.

* * * * *